(12) United States Patent
Linsen et al.

(10) Patent No.: US 7,430,485 B2
(45) Date of Patent: Sep. 30, 2008

(54) METHOD AND SYSTEM FOR ANALYZING COATINGS UNDERGOING EXPOSURE TESTING

(75) Inventors: Michael W. Linsen, North Wales, PA (US); Edward A. Schmitt, Richboro, PA (US); Mark Richard Schure, Blue Bell, PA (US)

(73) Assignee: Rohm and Haas Company, Philadelphia, PA (US)

( * ) Notice: Subject to any disclaimer, the term of this patent is extended or adjusted under 35 U.S.C. 154(b) by 233 days.

(21) Appl. No.: 10/868,287

(22) Filed: Jun. 15, 2004

(65) Prior Publication Data

US 2005/0043898 A1 Feb. 24, 2005

Related U.S. Application Data

(60) Provisional application No. 60/497,083, filed on Aug. 22, 2003.

(51) Int. Cl.
*G01N 37/00* (2006.01)
*G01N 33/00* (2006.01)
*G01N 31/00* (2006.01)

(52) U.S. Cl. ....................................................... 702/81
(58) Field of Classification Search .................... 702/81
See application file for complete search history.

(56) References Cited

U.S. PATENT DOCUMENTS

| | | | |
|---|---|---|---|
| 4,139,107 A * | 2/1979 | Ninomiya et al. ............ | 414/392 |
| 4,615,902 A | 10/1986 | Alman et al. | |
| 5,001,353 A | 3/1991 | Odake et al. | |
| 5,831,725 A | 11/1998 | Lee | |
| 6,043,894 A | 3/2000 | Anderson et al. | |
| 6,459,477 B1 | 10/2002 | Berlin et al. | |
| 2007/0078609 A1* | 4/2007 | Subramanian et al. ........ | 702/27 |

FOREIGN PATENT DOCUMENTS

| | | | |
|---|---|---|---|
| EP | 0 117 390 A | | 9/1984 |
| EP | 1146330 | * | 10/2001 |
| EP | 1 229 321 A | | 8/2002 |
| EP | 1 508 796 | * | 2/2005 |
| JP | 06148005 A | | 5/1994 |
| JP | 08334320 A | | 12/1996 |
| JP | 09061388 A | | 3/1997 |
| JP | 09189664 A | | 7/1997 |
| JP | 11211673 A | | 8/1999 |
| JP | 2000/065750 A | | 3/2000 |
| JP | 2000/121631 A | | 4/2000 |
| JP | 2002/139452 A | | 5/2002 |
| JP | 2002/181734 A | | 6/2002 |
| WO | WO 98 16815 A1 | | 4/1998 |
| WO | WO 98 36240 A1 | | 8/1998 |
| WO | WO 02/13136 A | | 2/2002 |

* cited by examiner

*Primary Examiner*—Michael Nghiem
(74) *Attorney, Agent, or Firm*—Tifani Cottingham

(57) ABSTRACT

A method and system for analyzing a plurality of coatings undergoing exposure testing is disclosed. Included in the system are a data acquisition system and a computer system. The data acquisition system acquires coating identification and attribute data through various input devices, while the computer system automatically receives, stores, analyzes and displays the coating attribute data. The analytical results relate to the durability of a coating composition under test, which may be used for predicting the performance of a coating characteristic and developing improved coating compositions.

14 Claims, 6 Drawing Sheets

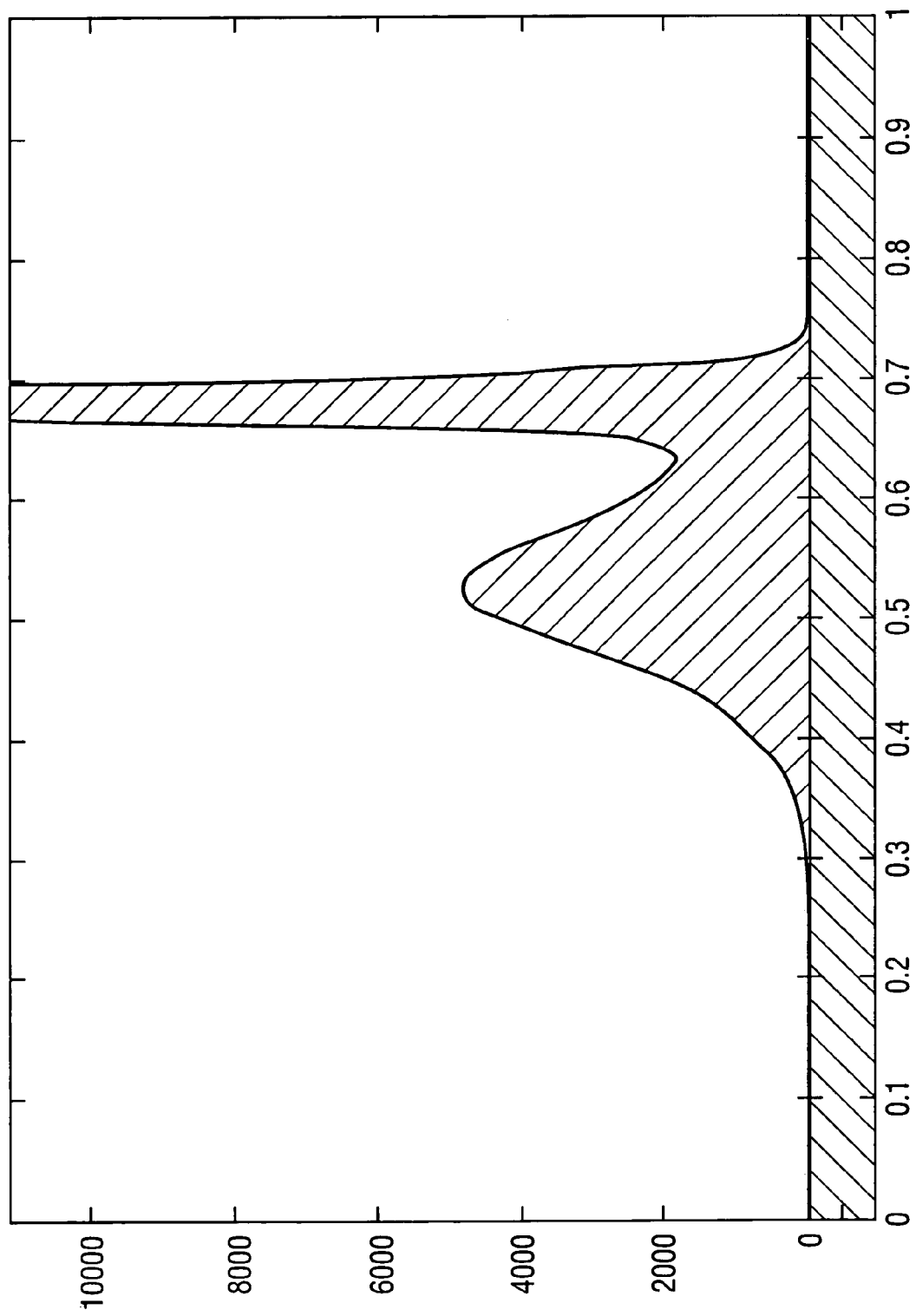

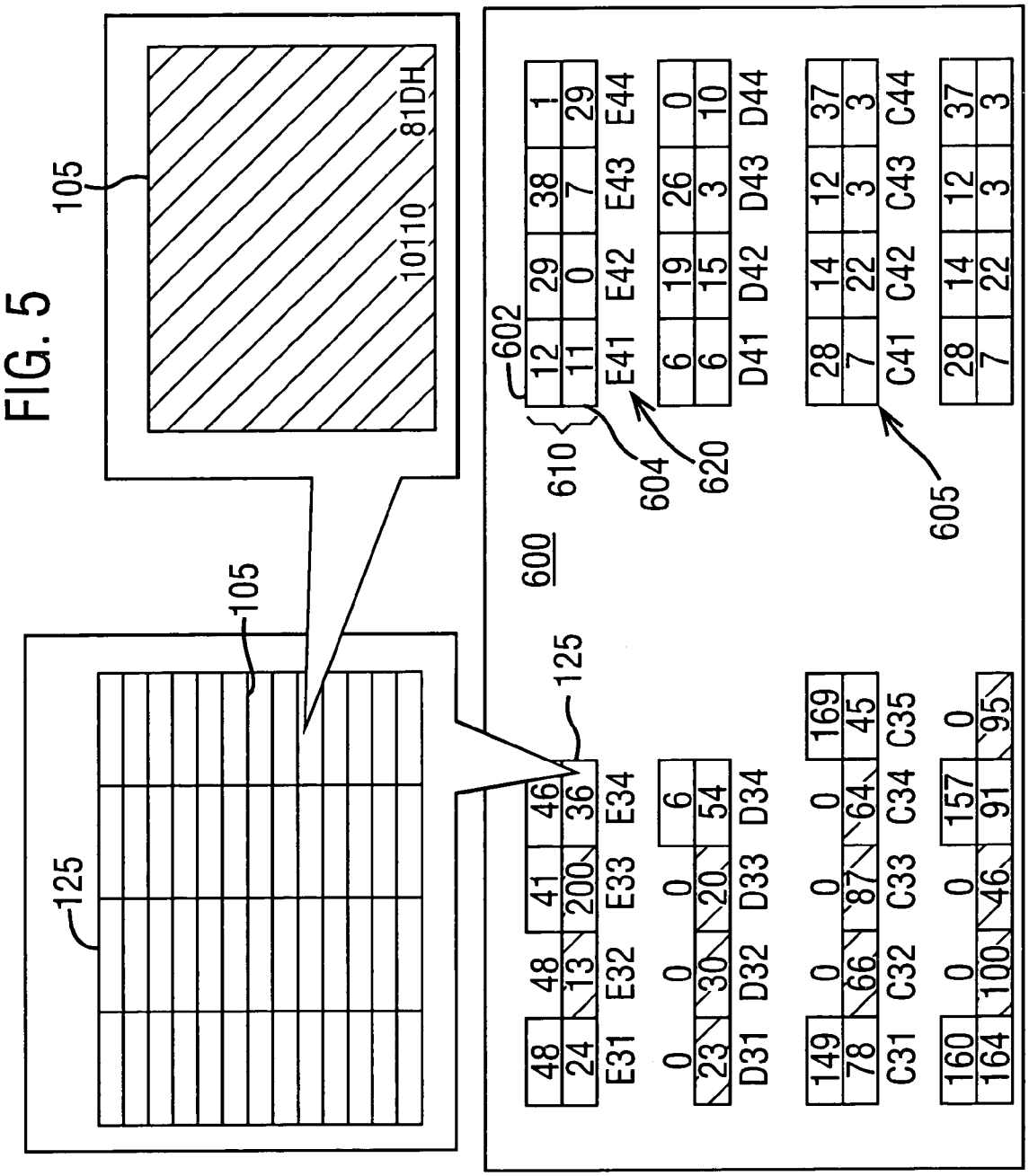

METHOD AND SYSTEM FOR ANALYZING COATINGS UNDERGOING EXPOSURE TESTING

CROSS REFERENCE TO RELATED PATENT APPLICATIONS

This is a non-provisional application of prior pending U.S. provisional application Ser. No. 60/497,083 filed on Aug. 22, 2003.

BACKGROUND

This invention relates to a method and system for analyzing coatings undergoing exposure testing, and more particularly, to a method and system for automatically acquiring, storing, analyzing, and displaying quality data relating to paint compositions undergoing outdoor exposure testing at various test sites.

Traditional analysis of indoor and outdoor paint test panels, referred to as exposure series testing, uses a manual and time-consuming process for generating data to judge paint durability. While color and gloss meter instruments may be used to generate some coating attribute data, often this data is manually acquired and manually recorded into a database for subsequent analysis. Other coating attribute data, such as cracking, flaking, and mildewing, for example, are subjective in nature, making them prone to variation depending on the tester's observation and interpretation. Yet other coating attribute data, such as reflectivity spectra, for example, is complex in nature, making it cumbersome for manual transcription. This traditional procedure, being dependent on the skill level of the tester, is not only time-consuming, but is also subject to systemic errors, including but not limited to, inaccurate data reading, incorrect data entry, and incorrect association of acquired data to test panel subject. Also, with a highly manual process, limited discrete data points may be acquired in a defined time window, which limits the quality of interpolated and extrapolated test data. In an effort to resolve some of these manual data entry issues in measuring painted test panels, an automated method and device has been described in U.S. Pat. No. 6,459,477, which involves measuring a coating property on a test panel by manipulating the panel before a measuring device, performing an instrument reading, and returning the test panel to its original location. However, such a painted test panel measuring method does not address all of the concerns and interests associated with multiple and different coating compositions undergoing exposure testing at various test sites in different geographic regions.

In an effort to advance materials analysis, well known image analysis techniques for characterizing materials have been applied to weathered materials. However, it is very difficult to analyze large numbers of materials efficiently because it is not practical to move large numbers of samples from an exterior placement to the laboratory for analysis, and then back out to their correct exterior placement. Such a process is logistically difficult and time consuming, and the handling may even cause damage to the materials undergoing testing.

Accordingly, there remains a need in the art for a paint exposure analysis system that provides for a greater degree of quantitative data entry and comparative analysis among and between multiple test samples undergoing exposure testing at widely dispersed test sites as well as a means to manage the physical inventory thereof. The system proposed herein provides such a system.

STATEMENT OF THE INVENTION

In a first aspect, there is provided a coating analysis system including a data acquisition system and a computer system. The data acquisition system is adapted to objectively acquire and store in digital form an identification code relating to a set of test samples of coating compositions undergoing an exposure test and coating attribute data relating to the set of test samples, the set of test samples being one of multiple sets of test samples. The computer system includes a computer and a storage device. The computer is programmed for receiving data from the data acquisition system, the data including the test sample identification code and the coating attribute data from the multiple sets of test samples, storing and retrieving the test sample identification code and the coating attribute data at a database at the storage device, analyzing the coating attribute data, and generating an output representative of the quality of the coating composition.

In another aspect, there is provided a method of analyzing a coating that includes objectively acquiring a test sample identification code relating to a set of coating compositions undergoing an exposure test, the set of coating compositions being one of a multiple of sets of coating compositions, objectively acquiring coating attribute data relating to a coating composition in the identified set and automatically storing the data in digital form, populating a database with temporal entries of the coating attribute data, analyzing the coating attribute data, and generating an output representative of the quality of the coating composition.

In a further aspect, there is provided a coating composition made using the method described above.

As herein disclosed, use of a robust coating analysis system and method that augments human subjective data with instrument read data promotes the development of coating compositions having high quality characteristics by providing mass quantities of high resolution temporal data that may be utilized for predictive analysis purposes, especially when used as herein disclosed and contemplated.

BRIEF DESCRIPTION OF THE DRAWINGS

Referring to the exemplary drawings wherein like elements are numbered alike in the accompanying Figures:

FIGS. 3 and 4 depict exemplary graphical information resulting from an application of the system of FIG. 1. In FIG. 3, the x axis is the Pixel Intensity and the y axis is the Pixel Count. In FIG. 4, the x axis is the Crack Area (Pixel Count) and the y axis is the Crack Count; and FIG. 5 depicts an inventory map for use in an embodiment of the invention.

DETAILED DESCRIPTION

Figure 1:
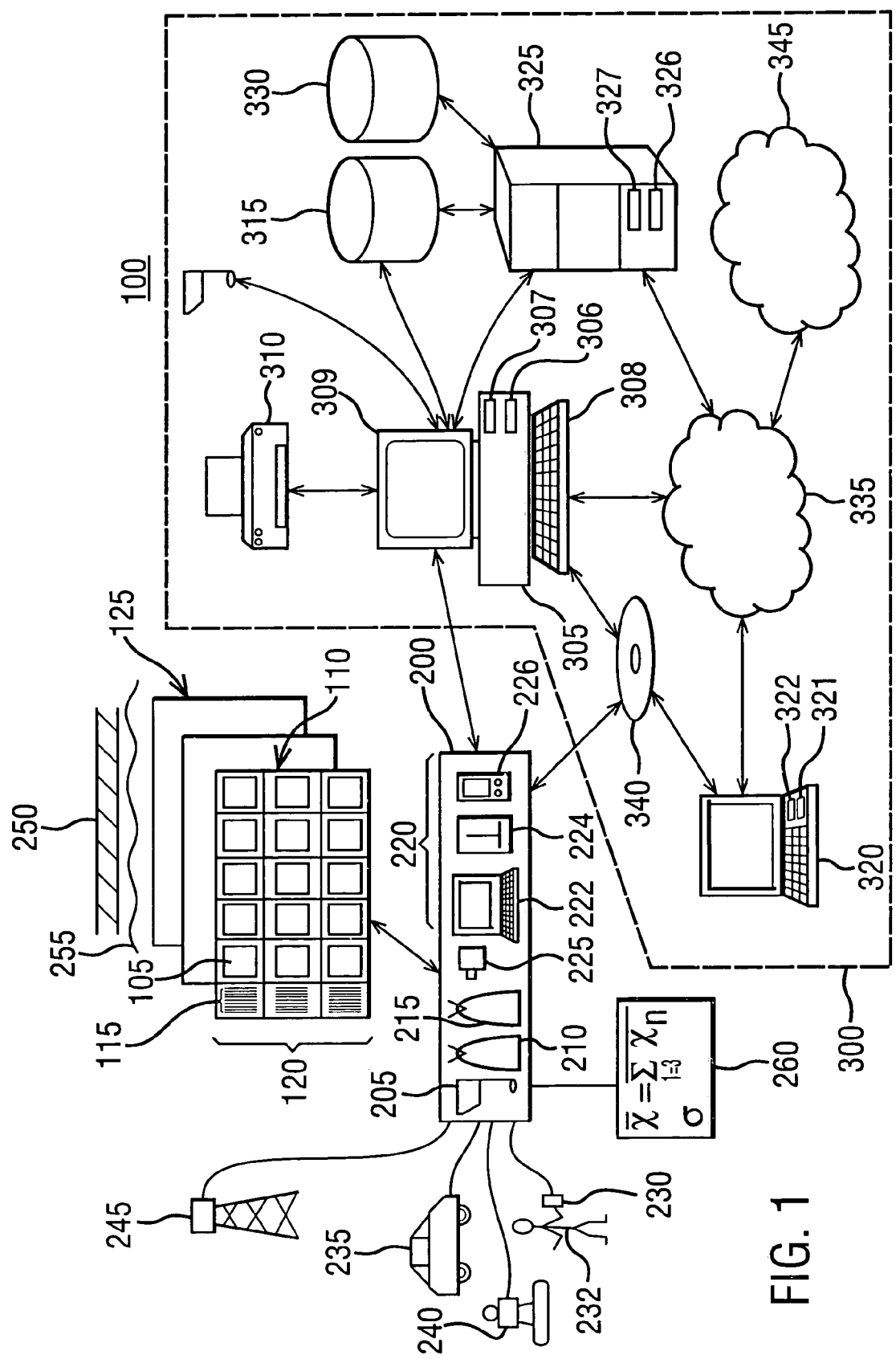
FIG. 1 depicts an exemplary coating analysis system in accordance with an embodiment of the invention.
Figure 2A:
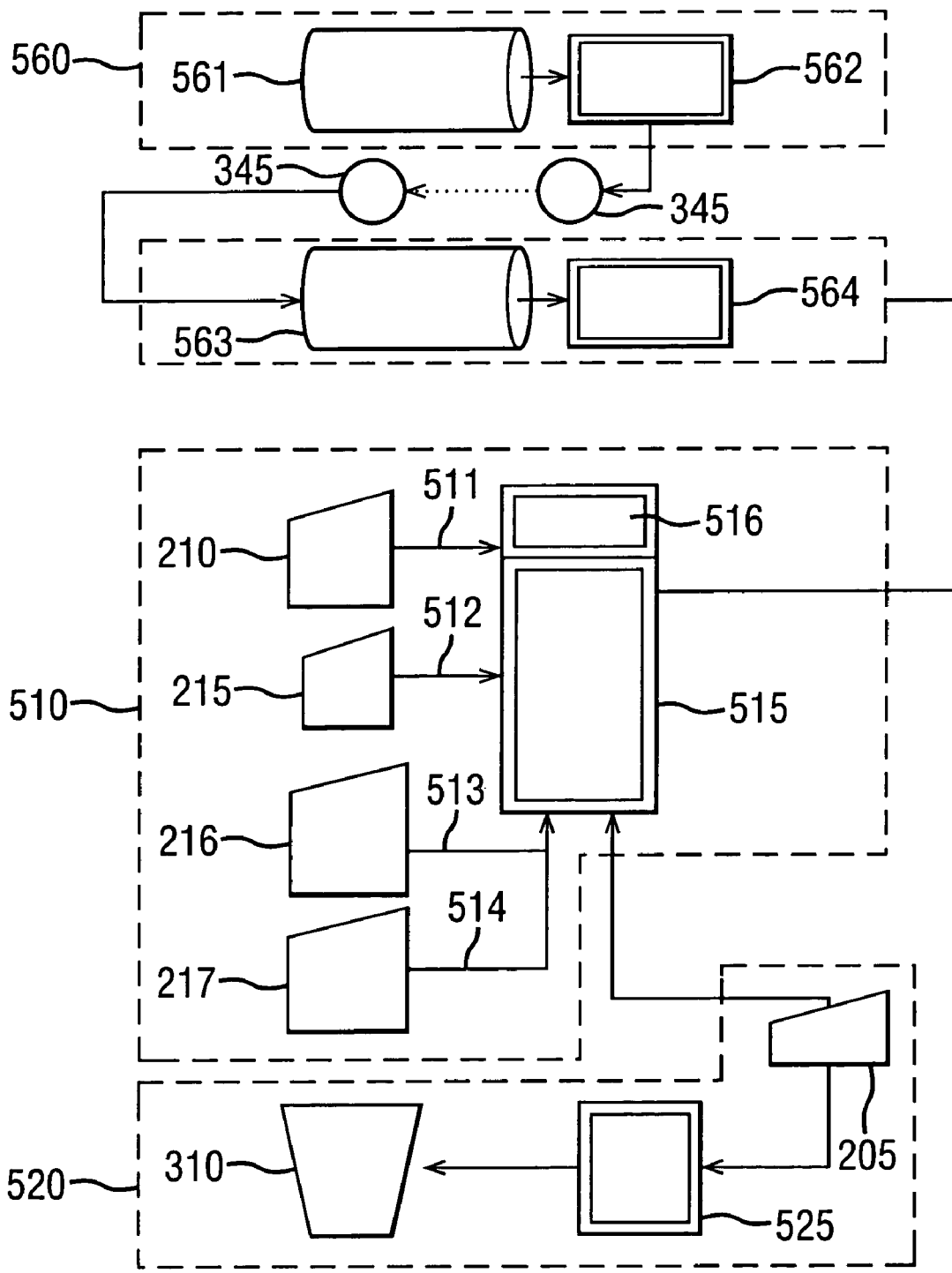
FIG. 2 depicts an exemplary system architecture for managing the flow of data with the system of FIG. 1.
Figure 2B:
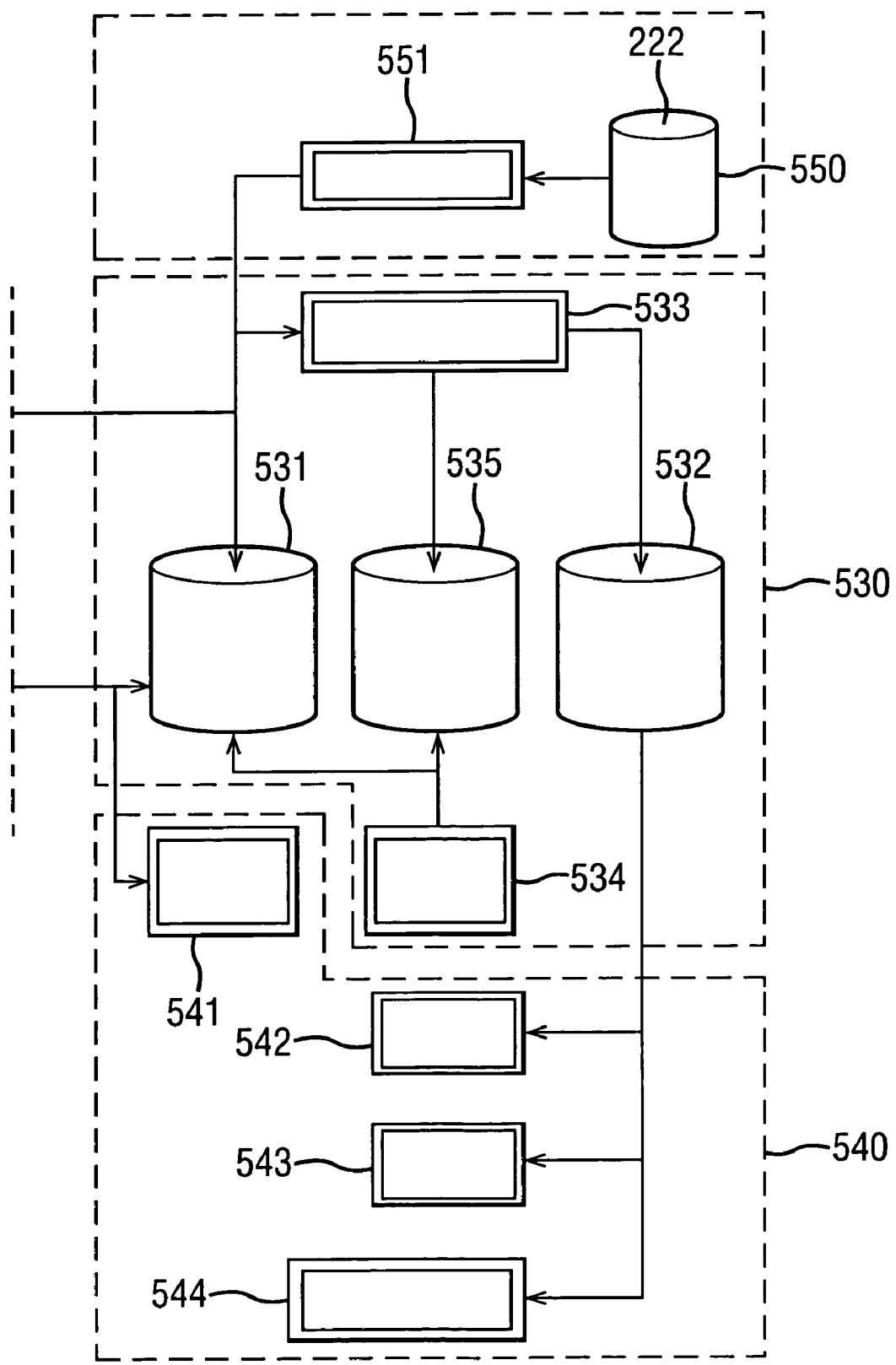

As disclosed herein, FIG. 1 depicts a schematic view of an exemplary coating analysis system 100 for acquiring, storing and analyzing objective data relating to a coating composition undergoing exposure testing, and FIG. 2 depicts a schematic view of an exemplary system architecture 500 for managing the flow of data within system 100.

In an embodiment and referring now to FIG. 1, coating analysis system 100 includes a data acquisition system 200 and a computer system 300. In a broader sense, data acquisition system 200 is both a data acquisition system and a data management system, but will be referred to herein as a data acquisition system. Data acquisition system 200 is configured for objectively acquiring a test sample identification code 115, such as a bar code for example, and for objectively acquiring and managing coating attribute data relating to a fixed test sample 105, and computer system 300 is configured for storing and analyzing the acquired data in digital format. As used herein, the term "objectively acquiring" refers to the acquisition of data in the absence of human subjective interpretation. Each test sample 105 may be arranged in a set of test samples 110 having a test sample identification code 115, such as a bar code (hereinafter "bar code" 115), or each test sample 105 may be arranged individually with its own bar code 115. In this manner, the term "set of test samples" refers to one or more test samples. Each set of test samples 110 may be arranged on a board or a panel 125 in an array of test samples 120. The panels 125 of test samples are typically arranged in rows and columns in a test area, such as an outdoor field for example, thereby providing a plurality of test samples for exposure testing with each test sample having an associated bar code 115. An exemplary identification code includes a bar code, but may be any identification coding scheme suitable for the purpose of identifying each test sample 105 and the site at which each test sample 105 is undergoing exposure testing. In an embodiment, test sample set 110 includes 5 individual test samples 105, but alternative embodiments may include any number of individual test samples 105. The panels 125 of test samples may be arranged in either an open area exposed to the elements of nature, or in a closed area exposed to controlled elements. Multiple test sites may be employed at various geographic areas, thereby providing a variety of test data where the test samples are exposed to substantially different forces and elements of nature. The coating attributes that are viewed, acquired, analyzed and reported may include color reflectance, reflectance spectra, angular reflectance, color coordinates (L-lightness, a-red/green, and b-yellow/blue), color transmission, color absorption, color scattering, coating gloss, subjective attributes, and machine-derived objective attributes, for example. However, other coating attributes may be viewed, acquired, analyzed and reported as appropriate. The term color reflectance refers to measurements over the color reflectivity spectra, which includes, for example, 31 color reflectance measurements from 400 nanometers (nm) to 700 nm at 10 nm intervals. Drop-down menus, discussed below, control which color reflectance measurements are enabled or disabled. The term paint gloss refers to gloss readings at an angle relative to a plane parallel to the coated surface, such as at a 20-degree angle, a 60-degree angle, or an 85-degree angle, for example. However, other gloss reading angles may be employed as appropriate. The terms subjective and machine-derived objective attributes refer to qualitative representations of surface rust, chalking, checking, cracking, erosion, blistering, flaking, corrosion, dirt, mildew, adhesion, and scum, for example. While embodiments disclosed herein may refer to paint as an exemplary coating composition undergoing exposure testing, it will be appreciated that the teachings of the invention are also applicable to other coating compositions, such as a stain for example.

Data acquisition system 200 may include any number of the following input devices: a test sample identification reader 205, such as a bar code scanner for example; a color meter 210, such as the Miniscan XE Plus Color meter manufactured by Hunter for example; a gloss meter 215, such as a QIP gloss meter manufactured by Quality Imaging Products, Inc., or a BYK-Gardener gloss meter manufactured by BYK-Gardner Gmbh, for example; a data entry device 220, such as a portable computer 222 (such as a laptop computer, a notebook computer, or any other non-stationary computing device capable of data entry), a tablet computer 224, and a personal desktop assistant (PDA) 226, for example; and, a digital camera 225. Data acquisition system 200 includes application software for acquiring and storing test sample bar code 115 and data, discrete or temporal, relating to various attributes, discussed above, of test sample 105 undergoing exposure testing. In an embodiment, data acquisition system 200 includes any number and combination of the aforementioned input devices arranged in signal communication with portable computer 222, which is adapted to run application software, discussed further below, thereby enabling automated data entry and data transfer to a host computer 305, discussed further below.

An exemplary data acquisition system 200 may be arranged as: a portable carrying device 230, such as a backpack to be carried by a person 232 for example; a mobile device 235, such as a push and/or pull cart, a self-powered device, or a motor vehicle (wheeled or having any other traction means), for example; a robot device 240; or, a stationary tower-mounted Lidar (light detection and ranging) device 245. Mobile device 235 may be driven by a person on a road between and among test samples 105, or may be self-directed along a track 250 or via underground self-guiding wire 255. Robot device 240 may also follow track 250 or underground self-guiding wire 255, or may alternatively be programmed to follow a predefined path between and among test samples 105. Robot device 240 may be remote controlled or self-controlled via an onboard programmed controller. Tower-mounted device 245 may be operable to view many test samples 105 by employing a programmed controller and a multi-axis swivel head for mounting a Lidar transceiver. In an embodiment, each device employing data acquisition system 200 is adapted and operable to acquire and store data from a plurality of test samples 105.

An exemplary computer system 300 includes a host computer 305, a printer 310, and a storage device 315. Host computer 305 may include a storage medium (such as a memory) 306, a processing circuit (such as a processor) 307, an input/output device (such as a keyboard and a mouse for example) 308, and a display 309. Printer 310 is representative of a printer that is capable of printing an output such as a barcode, an alpha-numeric file, or a graphic file; however, other printers may be employed as appropriate. Other computers, such as a laptop computer 320 and a server 325, for example, may be arranged in signal communication via wire or wireless with host computer 305. Laptop computer 320 and server 325 may include a storage medium 321, 326 and a processing circuit 322, 327, respectively, that includes application software, stored at memory 321, 326 and executed at processor 322, 327, for communicating with host computer 305 and for storing and analyzing the acquired data. A second storage device 330 may be employed for backup or for global access purposes, and multiple devices may be interconnected via an Internet or other network connection 335. While reference is made herein to a laptop computer 320, it will be appreciated that any computing device serving the purpose of a portable computer may be substituted therefore. Similarly, while reference is made herein to a server 325, it will be appreciated that any computing device capable of providing the service of a server may be substituted therefore.

Remotely acquired data may be communicated as a stream of data from data acquisition system 200 to host computer 305 directly via wire or wireless, or from data acquisition system 200 to a writeable media 340, such as a floppy disk, a compact disc, or a PCMCIA (Personal Computer Memory Card International Association) card, for example, or from laptop computer 320 via writeable media 340 or network 335, such as the Internet or Intranet for example, or from a remote acquisition communication system 345, such as email for example.

In general, more than one data acquisition system may be connected to more than one computer, storage device, and database, through a plethora of different connections, including USB (Universal Serial Bus), serial, Firewire, wireless, Ethernet, or any other suitable communication arrangement. Exemplary software employs user interface techniques such as drop-down menus and point-and-click mechanisms. Data acquisition systems, including image acquisition systems, and image processing software, described further below, are interconnected to system computers and servers, thereby allowing a host of different analysis configurations and database services. An exemplary image analysis includes the automatic determination of surface cracking or flaking from an image. Other image analyses may include statistical analysis, chemometric analysis, correlation analysis, covariance analysis, or any other analysis suitable for image data evaluation.

More specifically, and in an exemplary embodiment, host computer 305 includes application software (the Application Software), stored at memory 306 and executed at processor 307, for receiving, storing, analyzing, and displaying data acquired from data acquisition system 200. In an exemplary embodiment, the Application Software includes a graphical user interface (GUI) employing GUI techniques, such as icons, drop-down menus, radio buttons, selection tabs, input boxes, scroll windows, action buttons, and check boxes, for example. In an alternative embodiment, host computer 305 includes application software for receiving the acquired data from data acquisition system 200, communicating with server 325, and displaying analysis results, and server 325 includes application software, stored at memory 326 and executed at processor 327, for communicating with host computer 305 and for storing and analyzing the acquired data. In either embodiment, host computer 305 may include user interface software for enabling the user to manage the flow of data from data acquisition system 200 to and from databases at storage devices 315, 330, where the acquired data is stored for subsequent analysis. In an embodiment, the Application Software includes image recognition software that is capable of processing image data acquired by digital camera 225 and providing an objective representation of a coating attribute. For example, a numerical count of contiguously arranged abnormally colored pixels may be representative of the degree of surface cracking or flaking.

The Application Software at host computer 305, or alternatively at server 325, is programmed for: periodically receiving the test sample bar code 115 and the coating attribute data from data acquisition system 200, thereby providing temporal data entries; storing and retrieving the bar code and coating attribute data at a database at storage device 315; replicating all or selected portions of the coating attribute data at the first database at storage device 315 and storing it to the second database at storage device 330; managing the flow of data to and from the first and second databases at storage devices 315, 330, respectively; viewing the contents of the first and second databases; analyzing the coating attribute data; and, generating a text file, a graphic file, or an exposure test report representative of the quality of the coating composition, which may include discrete data, temporal data, or both. As discussed above, the bar code and coating attribute data may be received at host computer 305 from a remotely operated data acquisition system 200. Analysis of the coating attribute data may include a correlation analysis that relates a first coating attribute data to a second coating attribute data (such as paint gloss at a 20-degree angle as a function of chalking, or paint color reflectance as a function of erosion, for example), or a temporal analysis that tracks a set of coating attribute data (such as paint gloss at 20, 60 and 85-degree angles, for example) over time.

An exemplary system architecture 500 used in conjunction with the Application Software for managing the flow of data among and between the various elements of coating analysis system 100 will now be described with reference to FIG. 2, which depicts an arrangement of program modules that form the Application Software executed at processor 307. Each program module is designated as a "double-walled-box" in FIG. 2, activated by a GUI icon, and discussed separately below.

The acquisition of coating attribute data is represented at block 510, which in an embodiment includes inputs from a color meter 210, such as a Hunter Color Meter for example, a gloss meter 215, such as a QIP Gloss Meter for example, and other gloss meters 216, 217, such as BYK-Gardner Gloss Meter #1 and BYK-Gardner Gloss Meter #2 for example. While an embodiment of the invention is depicted employing designated color and gloss meters, it will be appreciated that such designation is for exemplary purposes only, and that other meters for measuring color, gloss, or any other coating attribute, may be employed as desired. While only four input paths 511, 512, 513, 514 are depicted in FIG. 2, it will be appreciated that these inputs are exemplary only and that other input paths may be available as discussed above in reference to the input devices of data acquisition system 200. In general, data acquisition software takes color, gloss, and other optical data and stores the data in a manner suitable for incorporation into a database. More specifically, and in an exemplary embodiment, a user launches a Data Acquisition Program (DAP) 515 by selecting an DAP launch icon on the display of portable computer 222, which runs the color and gloss meters 210, 215, 216, 217 in an automated manner. Similar to DAP 515, each program of system architecture 500 may be launched by using a GUI icon. Also providing input to DAP 515 is bar code scanner 205, which is part of bar code system 520 along with a Bar Code Printer Program 525 and bar code printer 310. The user uses bar code scanner 205 to read a bar code 115 into DAP 515. Other user identification (ID) and/or password entries may be entered into DAP 515 prior to data acquisition for purposes of quality control and user tracking. The user then selects an appropriate data acquisition mode, such as, read color and gloss meters and digital camera, read color and gloss meters only, read color meter only, or read gloss meters only, for example, and then proceeds to acquire the desired coating attribute data sets, with each new data set being preceded by a bar code scan. Prior to data acquisition at color meter 210, the user may run a calibration routine that uses a black and white standard. Statistical data entry 260 may be optionally selected at data acquisition system 200 by choosing an appropriate selection from a drop-down menu. While in statistical data entry mode 260, three measurements are taken, for example, from which an average (x-bar) and a standard deviation (sigma) is calculated for each coating attribute under analysis. For subjective data entry, speech recognition software may be used to enter the subjective rating. All acquired data is temporarily stored at data acquisition system 200 for subsequent transfer to storage device 315.

In an exemplary data acquisition system 200 that is in direct signal communication with host computer 305, the Application Software automatically writes the acquired data into a database 531 (See Block 530) at storage device 315, which may be verified by using a Database Visualizer Program 541. Upon completion of the data set entries, the user may automatically replicate the data into a globally-accessible database 532 at storage device 330 by using a Replicator Program 533. The contents of database 532 may be verified by using another Database Visualize Program 543. As used herein, direct signal communication means that data acquisition system 200 is in wired or wireless communication with host computer 305 during data acquisition.

In an embodiment where data acquisition system 200 is not in direct signal communication with host computer 305, acquired data may be stored at portable computer 222 and then downloaded to host computer 305 by copying to and reading from a compact disc (CD) 340, by connection via a network 335, by email communication 345, or by any other suitable data transport device, such as a memory stick or flash memory, for example. The acquired data stored at portable computer 222 is automatically merged with the contents of database 531 by running a Merge-to-Database Program 551 (See Block 550), and then the Replicator Program 533 is run to automatically copy the data into database 532.

In an embodiment where remotely acquired data is stored in spreadsheet form 561 (See Block 560). and communicated to host computer 305 via email communication 345, coating analysis system 100 uses a Data Verification Program 562 to automatically verify the data for proper number placement, proper syntax, and proper lexicography prior to populating database 531 with data, and uses a Conversion Program 564 to automatically take the data out of the verified spreadsheet 563 and enter it into database 531. As before, the user then runs the Replicator Program 533 to automatically copy the data into database 532. Data Verification Program 562 flags illegitimate data and issues diagnostic routines, thereby automatically ensuring legitimate data at the entry point to database 531.

An exemplary Data Mining Program 544 (See Block 540). takes data from database 532 and organizes the data for analysis, which may include correlation analysis given two or more types of tests or attributes. The analytical results may then be graphed. In an embodiment, Data Mining Program 544 finds all readings of a specified test series, grabs the attribute descriptors specified by the user, and arranges the data graphically. A correlation analysis graph may depict one coating attribute against another, or may depict the variation of one or more attributes over time.

An exemplary Mirror Program 534 is used in an embodiment to compare data between mirrored fields in database 531 and database 535, which is used for quality assurance and data legitimacy. A Database Visualize Program 542 is used in an embodiment to obtain table information from database 532.

Multiple databases 531, 532, 535 and multiple database visualization programs 541, 542, 543 are depicted for exemplary purposes only, which one skilled in the art will appreciate, may or may not be employed as depicted, and may be employed in alternative arrangements.

An exemplary Mirror Program 534 is used in an embodiment to compare data between mirrored fields in database 531 and database 535, which is used for quality assurance and data legitimacy. A Database Visualize Program 542 is used in an embodiment to obtain table information from database 532. Multiple databases 531, 532, 535 and multiple database visualization programs 541, 542, 543 are depicted for exemplary purposes only, which one skilled in the art will appreciate, may or may not be employed as depicted, and may be employed in alternative arrangements.

Databases 531, 532, 535 may be constructed to allow a multidimensional data warehouse to be constructed with automatic procedures in place to accomplish the warehousing during the evening on an off-line basis. In this manner, data mining may proceed automatically on the warehouse with automatic notification when there is a significant change in the analysis results. The integrity of the data in databases 531, 532, 535 may be preserved through the use of time stamping and high security log files.

An exemplary application of coating analysis system 100 involves the automated analysis of paint films undergoing either indoor or outdoor exposure testing, as discussed above. In an exemplary outdoor arrangement, panels 125 of test samples are arranged in rows in a field or other outdoor test area, with each panel 125 having a plurality of sets of test samples 110. A weather resistant bar code 115 identifies each test sample 105 on each panel 125. The user systematically inputs the coating attribute data by scanning the bar code 115 and each associated test sample 105 with one or more desired input device, and then repeats the process until the desired data on each test sample 105 has been taken. The Application Software installed on portable computer 222 enables the user to automatically insert the paint attribute data, such as color data, gloss data, reflectivity data, and digital images, for example, into a memory at portable computer 222, and to subsequently automatically insert the saved attribute data into database 315. The Application Software installed on host computer 305 enables the user to automatically receive the paint attribute data from portable computer 222, to analyze the data, and to display the analysis results. The Application Software may also include speech-recognition software for registering a voice-commanded subjective data entry, such as a verbal rating representative of the degree of chalking for example, and image processing software for creating a machine-derived objective data entry, such as that discussed above in reference to abnormally colored pixels for example. Optical images taken by digital camera 225 may be stored at and retrieved from database 531, and machine vision software may be employed in conjunction with the digital images to provide machine-estimated values that further characterize the mode and degree of paint degradation upon exposure to weathering conditions. Digital camera 225 is especially suited for taking high quality images of materials undergoing external exposure testing and may include an illumination scheme employing an auxiliary light source and baffles or shields to prevent shadows and to control light exposure. Exemplary auxiliary light sources may include an electronic flash, a light emitting diode, or any other suitable light source. Natural light, auxiliary light, baffles, diffusers and other optical elements, may be employed in combination to evenly illuminate the material being imaged. Furthermore, digital camera 225 is light weight and portable such that it may be hand held for the purposes of collecting digital images or it may be mechanically translated across the materials undergoing exposure testing using a motorized x-y stage, depicted generally at motor vehicle 235. In alternative embodiments, data acquisition system 200 may be carried via a backpack 230 and operated from the backpack 230, may be transported by a robot 240 and automatically operated via a programmable controller at the robot 240, may be stationary at a tower 245 and operated via a programmable controller and Lidar device at the tower 245, or may be operated from motor vehicle 235, which is guided by a track 250 or underground self-guided wire 255. Data acquired by data acquisition system 200 may be communicated to host computer 305 via wire, wireless, writeable media 340, or any other suitable communication means. Data mining software included with the Application Software enables the user to extract, analyze and display quality data relating to the paint composition, such as two-variable correlation analysis and temporal variation analysis, for example. Predictive software enables both extrapolation-based parametric predictions and pattern recognition-based nonparametric predictions, and decision-based software using fuzzy logic enables contextual deduction of paint performance.

Figure 4:
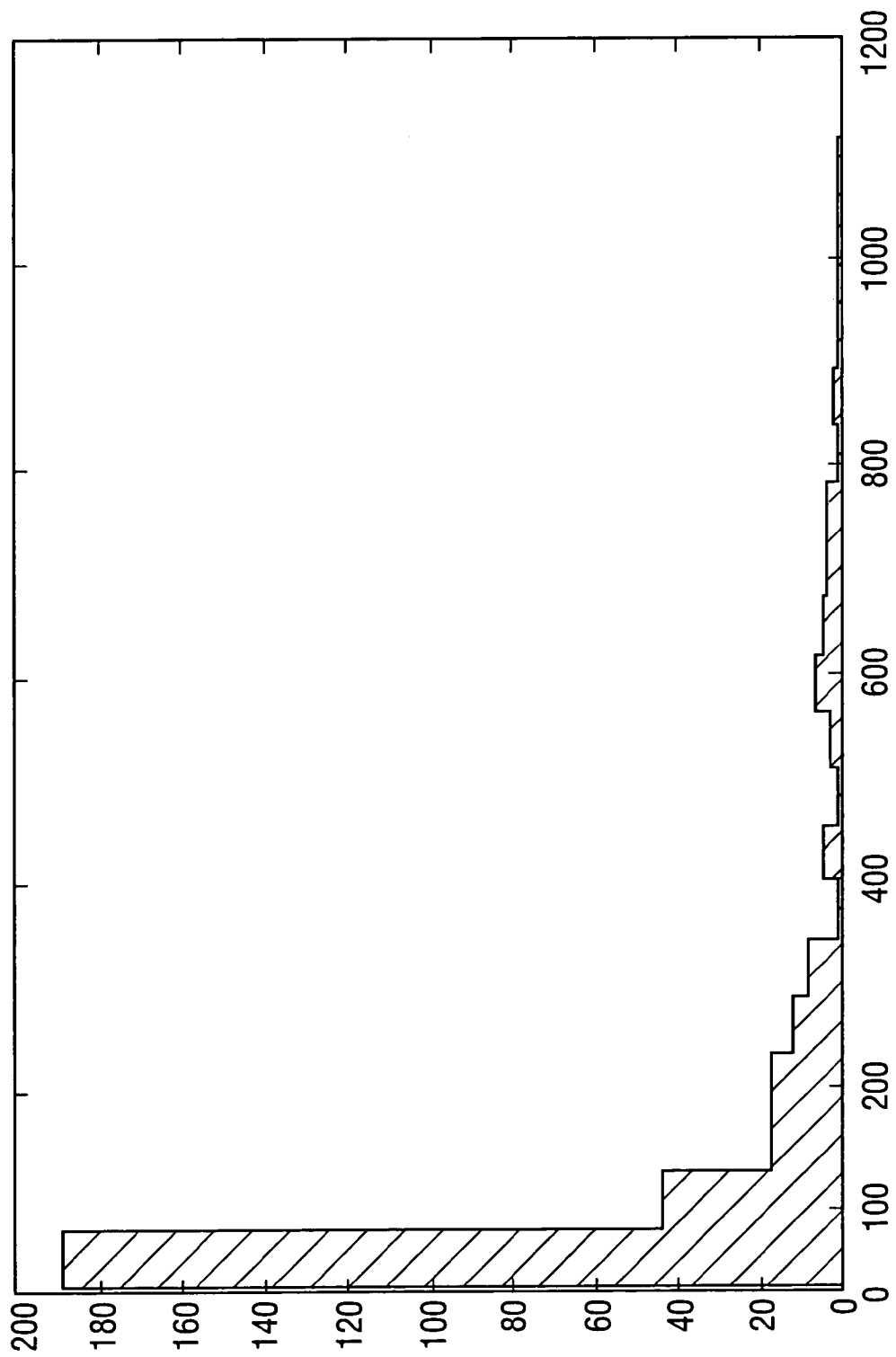

Reference is now made to FIGS. 3 and 4, which depict graphical results of exemplary attribute data analyses. The machine vision software referenced above may automatically interpret the image by identifying distinct features, classifying each feature, and then characterizing the features both individually and collectively. In FIG. 3, pixel count as a function of pixel intensity is depicted for a test sample 105, where the pixel intensity threshold (depicted in FIG. 3 as a pixel count in excess of 10,000 at a pixel intensity of approximately 0.69 (69%)) is determined from the distribution of pixel intensities provided by a digital image of sample 105. A change in color intensity, which is related to pixel intensity, of sample 105 over time may be analytically determined and graphically displayed by comparing and charting the pixel intensity threshold as a function of time. In FIG. 4, the number of cracks (crack count) as a function of crack area (pixel count) is depicted for a test sample 105. As depicted in FIG. 4, there are approximately 190 cracks with a crack area of about 50 pixels, approximately 40 cracks with a crack area of about 100 pixels, and approximately 15 cracks with a crack area of about 150 pixels, for example. A change in crack count or crack area of sample 105 over time may be analytically determined and graphically displayed to show the degree of paint degradation over time. In the analysis relating to FIG. 4, the optical image taken by digital camera 225 is converted to a black and white image and then inverted so that the cracks show up as white. The contiguous white pixels are then counted for each crack area and the results plotted in histogram form. By comparing large volumes of temporal data associated with a plurality of paint samples 105 that differ in coating composition, a user can efficiently determine those coating compositions that have superior quality characteristics.

Another aspect of the invention provides an inventory management system 516, embodied in software and accessible via host computer 305 for example, for managing the physical inventory of test panels 125 undergoing exposure testing, with each test panel 125 having multiple test samples 105. Test samples 105 are tracked physically over time by an inventory map 600, best seen by now referring to FIG. 5. Map 600 is representative of the status of multiple test panels 125 undergoing exposure testing, where the test panels 125 may be closely distributed, distributed over a large area, or distributed over multiple locations. By employing map 600, system 100 can objectively analyze sample performance and output performance as a function of time, location, and test conditions.

In an exemplary embodiment, numerical information provided by map 600 may be representative of the number of free space locations on test panel 125 or the number of actual test samples 105 on test panel 125, and color-coded information may be representative of the orientation of test panel 125 to the sun, or the type of test sample 105 undergoing test. Other attributes of test panel 125 may be represented by map 600 as desired.

Referring now to FIG. 5, an exemplary map 600 includes multiple pairs of boxes 610 arranged to represent a test fence 605 with each pair of boxes 610 having a coordinate designator 620, such as E41 for example. Each test fence 605 typically, but not necessarily, contains multiple test panels 125. In an embodiment, the top box 602 of each pair represents the north facing side of a test fence 605 and the bottom box 604 of each pair represents the south facing side of a test fence 605, with the contents of each box 602, 604 representing a particular attribute of an associated test panel 125, as discussed above. In the exemplary map 600 of FIG. 5, the numerical entry in each box 602, 604 represents the "free space" status of that particular test panel 125. For example, test panel 125 at coordinate location E34 has a numerical entry of 36, which represents 36 free space locations on that particular test panel 125. Also, a blue colored box may depict a test rack orientation, such as south facing at a 45 degree angle to vertical for example, and a white colored box may depict a different test rack orientation, such as north facing vertical or south facing vertical for example. Additional coloring, such as a red border for example, may depict additional attributes of a test fence. For example, a general configuration of a test fence, such as a test rack configured to hold 5 inch by 36 inch test panels with multiple test areas therein, may be depicted by no borders in map 600, while a test rack configured to hold individual test samples of dimension 4 inch by 12 inch, may be depicted by a red border in map 600. Bar code 115 associated with each test sample 105 provides a pointer to the database location, at database 531, 532 or 535 for example, where the attribute data of test sample 105 resides, which includes a location attribute that identifies the particular test panel 125, by coordinate location, that test sample 105 is a member of. If test sample 105 is moved from one test panel 125 to another, for reasons discussed below, the location attribute associated with test sample 105 is updated accordingly, thereby providing the user with up to date information regarding the location of each test sample 105.

Parameters that may be tracked as part of the physical asset may include: the name of fence 605; the location of fence 605, by coordinates for example; the location of panel 125, such as coordinate designator 620 for example; the barcode 115 associated with fence 605; the type of fence 650, such as standard panels, eves, aluminum panels, or tables, for example; the orientation of fence 605, such as north-vertical, south-45-degrees, hung-up, or hung-down, for example; the capacity of fence 605; the capacity used of fence 605; and, the capacity available of fence 605. Other parameters may be tracked as appropriate.

Parameters that may be tracked as part of the sample under test may include: a series name for a grouping of test panels 125; a panel descriptor for identifying a sub-set of a series of panels; a substrate identifier, such as pine (P), cedar (C), or aluminum (L), for example; a test area descriptor for identifying a test area on a panel; the orientation of test panel 125, such as north-vertical, south-45-degrees, hung up, or hung-down, for example; a unique barcode relating to a series, a panel, or a test area; the test initiation date; the reading schedule for the samples; and, the test results. Other parameters may be tracked as appropriate.

Sometimes it is desirable to have larger areas of contiguous test space made available than is currently available, such as when a new series of test samples 105 need to be tested reasonably dose to each other, or when data acquisition needs to be more efficiently organized, for example. Other times it may be desirable to merely reorganize the test panels 125 to reduce the amount of fragmentation of the available free space. Hence, test samples 105 may be moved from one test panel 125 to another in order to make a larger contiguous vacant area from many smaller vacant areas.

In determining how to move test samples 105, several factors may be considered, such as for example: the total number of contiguous free spaces needed; the amount of vacant area that currently exists or that is needed to form the large contiguous area; the amount of work the user is willing to expend in moving certain test samples; and, the distance that will be tolerated in moving a defined number of test samples for rearrangement. To assist in the decision making process, and in view of the distance-based coordinate system that map 600 is built on, optimization algorithms may be employed to make test sample moves via inventory management system 516 and to simulate moving test samples 105 under constraints to find an optimal number of moves to get the desired area. Such simulation constraints may include, for example: the maximum distance allotted for the total moves; the maximum number of moves; and, the number of test samples or test area that is allowed to move.

Algorithms for performing the test sample move simulations discussed above are similar to those commonly used for performing multidimensional optimization analyses. Such algorithms may include, for example: Linear Programning (LP) algorithms, which function under similar constraints to those listed above; Simplex methods; nonlinear least-squares methods; Karmarker's algorithm; simulated annealing algorithms; Genetic algorithms; and, Fuzzy optimization methods. Detailed descriptions of these algorithms and methods are available in various published text books and technical publications.

In an exemplary embodiment, inventory management system 516 utilizes the entire test sample location database, illustrated by map 600, and is usually run as a batch process. Upon completion of a simulation, the results are reported, and if the moves are utilized, the acceptance of the move operation enables the location attribute of each effected test sample 105 to be updated in the database automatically by inventory management system 516, without having to individually modify location information on each physical test sample 105. A result of using coating analysis system 100 is the acquisition and entry of objective data into an analytical database in an automated fashion, thereby avoiding time-consuming manual data entry and inconsistent subjective data entry, and providing improved data quality. Use of system architecture 500 in conjunction with coating analysis system 100 enables large amounts of data to be collected and managed in a rapid and efficient manner, thereby enabling high temporal resolution and accurate data extrapolation for improved predictive analysis. By configuring coating analysis system 100 to accommodate multiple input devices, to communicate with multiple peripheral devices and databases, and to communicate via multiple communication schemes, coating analysis system 100 is well adapted for expansion or reconfiguration as needed.

What is claimed is:

1. A coating analysis system, comprising:
    a data acquisition system adapted to objectively acquire and store in digital form an identification code relating to a set of test samples of coating compositions undergoing an exposure test and coating attribute data relating to the set of test samples, the set of test samples being one of multiple sets of test samples; and
    a computer system including a computer, a storage device and a storage medium, the storage medium, readable by a processing circuit, storing instructions for execution by the processing circuit for:
    receiving data from the data acquisition system, the data including the test sample identification code and the coating attribute data from a set of test samples;
    storing and retrieving the test sample identification code and the coating attribute data at a database at the storage device; and
    analyzing the coating attribute data and generating an output representative of the quality of the coating composition.

2. The coating analysis system of claim 1, wherein the data acquisition system comprises at least one of a test sample identification reader, a color meter, a gloss meter, a data entry device, and a digital camera, and is arranged as a portable carrying device, a mobile device, a self-powered mobile device, a motor vehicle, a traction vehicle, a controlled-path vehicle, a robot device, or a stationary device, wherein each device or vehicle is operable to acquire data from multiple test panels, each test panel having a plurality of sets of test samples arranged thereon.

3. The coating analysis system of claim 2, wherein the digital camera is arranged on a motorized x-y stage for mechanical translation across the set of test samples.

4. The coating analysis system of claim 2, wherein the data entry device comprises at least one of a portable computer, a laptop computer, a notebook computer, a tablet computer, and a personal desktop assistant.

5. The coating analysis system of claim 2, wherein the attribute of a coating composition includes at least one of a color reflectance reading, a gloss reading, and a subjective reading, the subjective reading including a qualitative representation of at least one of a surface rust, a chalking, a checking, a cracking, an erosion, a blistering, a flaking, a corrosion, a dirt, a mildew, an adhesion, and a scum condition.

6. The coating analysis system of claim 5, wherein:
    the gloss reading includes a gloss reading at an angle relative to a plane parallel to the test sample surface;
    the analyzing the coating attribute data includes performing a correlation analysis that relates a first coating attribute data to a second coating attribute data; and
    the storage medium further storing instructions for execution by a processing circuit for:
    processing image data acquired by the digital camera resulting in a machine-derived objective reading relating to the image data, the machine-derived objective reading including a qualitative representation of at least one of a surface rust, a chalking, a checking, a cracking, an erosion, a blistering, a flaking, a corrosion, a dirt, a mildew, an adhesion, and a scum condition.

7. The coating analysis system of claim 1, wherein the data acquisition system is in signal communication with the computer system.

8. The coating analysis system of claim 1, wherein the storage medium further stores instructions for execution by the processing circuit for:
    receiving the data from a remote data acquisition system by at least one of a wired connection, a wireless connection, a network connection, an Internet connection, an Intranet connection, and a data transfer medium.

9. The coating analysis system of claim 1, wherein the computer system further comprises:
    a server;
    a second storage device having a second database; and
    a printer adapted for printing at least one of a barcode, an alpha-numeric file, and a graphic file;
    wherein the server is in signal communication with the computer and at least one of the first database and the second database, and at least one of the computer and the server including a storage medium, readable by a processing circuit, storing instructions for execution by the processing circuit for:

replicating and storing at least a portion of the data stored at the first database to the second database;

managing the flow of data to and from at least one of the first and second databases;

viewing contents of at least one of the first and second databases; and analyzing the coating attribute data and generating an exposure test report.

10. The coating analysis system of claim 1, wherein the storage medium further stores instructions for execution by the processing circuit for:

analyzing and mapping the physical inventory of the multiple sets of test samples;

simulating a test sample move within the physical inventory; and reporting the results of the test sample move simulation.

11. A method of analyzing a coating, comprising:

objectively acquiring a test sample identification code, the identification code relating to a set of coating compositions undergoing an exposure test, the set of coating compositions being one of a multiple of sets of coating compositions;

objectively acquiring coating attribute data relating to a coating composition in the identified set and storing the data in digital form;

populating a database with temporal entries of the coating attribute data; and analyzing the coating attribute data and generating an output representative of the quality of the coating and further comprising:

verifying data entry of the acquired coating attribute data from a test site prior to populating the database with the data, the verifying including at least one of verifying proper number placement, verifying proper syntax, and verifying proper lexicography.

12. The method of claim 11, further comprising:

merging acquired coating attribute data from a first test site with acquired coating attribute data from a second test site at the database, the test sample identification code for each set of coating compositions including information relating to each respective test site.

13. The method of claim 12, further comprising:

replicating the data entry of the database at a second database, the second database having globally accessible data; and visualizing contents of at least one of the first database and the second database.

14. The method of claim 11, wherein the coating attribute data relates to at least one of a color reflectance reading, a gloss reading, a subjective reading, and a machine-derived objective reading, the subjective reading and the machine-derived objective reading each including a qualitative representation of at least one of a surface rust, a chalking, a checking, a cracking, an erosion, a blistering, a flaking, a corrosion, a dirt, a mildew, an adhesion, and a scum condition.

* * * * *